United States Patent
Yahav

(10) Patent No.: US 10,543,467 B2
(45) Date of Patent: Jan. 28, 2020

(54) DUAL COMPONENT APPLICATOR

(71) Applicant: Augma Biomaterials Ltd., Caesarea (IL)

(72) Inventor: Amos Yahav, Yeshuv Katzir (IL)

(73) Assignee: Augma Biomaterials Ltd., Caesarea (IL)

( * ) Notice: Subject to any disclaimer, the term of this patent is extended or adjusted under 35 U.S.C. 154(b) by 22 days.

(21) Appl. No.: 14/917,060

(22) PCT Filed: Sep. 4, 2014

(86) PCT No.: PCT/IL2014/050794
§ 371 (c)(1),
(2) Date: Mar. 7, 2016

(87) PCT Pub. No.: WO2015/036992
PCT Pub. Date: Mar. 19, 2015

(65) Prior Publication Data
US 2016/0213447 A1 Jul. 28, 2016

Related U.S. Application Data

(60) Provisional application No. 61/875,735, filed on Sep. 10, 2013.

(51) Int. Cl.
*B01F 15/02* (2006.01)
*A61C 5/50* (2017.01)
(Continued)

(52) U.S. Cl.
CPC ...... *B01F 15/0292* (2013.01); *B01F 13/0023* (2013.01)

(58) Field of Classification Search
CPC ........... A61C 5/04; A61C 19/005; A61C 5/60; A61C 5/62; A61C 5/64; A61C 5/68;
(Continued)

(56) References Cited

U.S. PATENT DOCUMENTS 2,591,046 A * 4/1952 Brown ................. A61M 5/284
222/136
3,016,896 A * 1/1962 Van Sickle ........... A61M 5/284
604/125

(Continued)

FOREIGN PATENT DOCUMENTS

EP 0072058 2/1983
EP 1437150 7/2004
(Continued)

OTHER PUBLICATIONS

Communication Relating to the Results of the Partial International Search dated Jan. 29, 2015 From the International Searching Authority Re. Application No. PCT/IL2014/050794.
(Continued)

*Primary Examiner* — Wade Miles
*Assistant Examiner* — Shannel N Wright

(57) ABSTRACT

A mixing applicator for mixing a fluid substance with a solid substance to obtain a resulting substance having a desired consistency, comprises: two valves slidably displaceable within a hollow elongated barrel and sequentially arranged along a longitudinal axis, the valves having a third cross-sectional shape being complementary to a first cross sectional shape, thereby providing fluid-tight engagement within the first cross-sectional shape, the third cross-sectional shape being mismatched with a second cross-sectional shape to form a mismatch zone along a length of a chamber, the mismatch zone allowing fluid flow around the valves, thereby to allow the two valves to effect mixing of the fluid substance with the solid substance and subsequently to remove excess fluid to obtain the resulting substance having the desired consistency.

16 Claims, 10 Drawing Sheets

(51) Int. Cl.
 *B01F 13/00* (2006.01)
 *B01F 15/00* (2006.01)
 *A61B 17/88* (2006.01)

(58) Field of Classification Search
 CPC .................... A61B 17/8825; B65D 81/32; B65D 81/3211; B65D 81/3255; B01F 15/0087; B01F 15/0237; B01F 15/0292; B01F 15/0023; A61M 2005/3132; A61M 5/2448; A61M 5/248
 USPC .............................. 604/77, 82–97; 600/191
 See application file for complete search history.

(56) References Cited

U.S. PATENT DOCUMENTS

| | | | | |
|---|---|---|---|---|
| 3,380,451 | A * | 4/1968 | Porter | A61M 5/284 604/90 |
| 4,185,740 | A * | 1/1980 | Perfect | A61C 5/64 206/220 |
| 4,496,344 | A * | 1/1985 | Kamstra | A61M 5/284 604/191 |
| 4,613,326 | A * | 9/1986 | Szwarc | A61M 5/284 604/218 |
| 4,747,829 | A * | 5/1988 | Jacob | A61M 5/322 604/110 |
| 4,792,329 | A * | 12/1988 | Schreuder | A61M 5/284 604/191 |
| 5,281,265 | A | 1/1994 | Liu | |
| 5,472,422 | A * | 12/1995 | Ljungquist | A61M 5/2448 604/518 |
| 5,549,561 | A * | 8/1996 | Hjertman | A61M 5/2448 222/136 |
| 5,605,542 | A * | 2/1997 | Tanaka | A61M 5/284 604/86 |
| 5,637,100 | A * | 6/1997 | Sudo | A61M 5/284 604/218 |
| 5,720,731 | A * | 2/1998 | Aramata | A61M 5/284 604/191 |
| 5,971,953 | A * | 10/1999 | Bachynsky | A61M 5/284 604/181 |
| 6,544,233 | B1 * | 4/2003 | Fukui | A61M 5/31596 604/191 |
| 7,371,408 | B1 | 5/2008 | Petersen et al. | |
| 7,371,409 | B2 | 5/2008 | Petersen et al. | |
| 7,371,410 | B2 | 5/2008 | Petersen | |
| 2002/0045865 | A1 * | 4/2002 | Mitomi | A61M 5/3134 604/207 |
| 2003/0167093 | A1 | 9/2003 | Xu et al. | |
| 2004/0020796 | A1 * | 2/2004 | Cheetham | A61C 5/64 206/63.5 |
| 2004/0236273 | A1 * | 11/2004 | Tanaka | A61M 5/284 604/89 |
| 2004/0254259 | A1 | 12/2004 | Ricci et al. | |
| 2007/0106210 | A1 * | 5/2007 | Fischer | A61C 5/62 604/82 |
| 2007/0161961 | A1 * | 7/2007 | Hasegawa | A61M 5/3134 604/187 |
| 2009/0018496 | A1 * | 1/2009 | Harper | A61M 5/31596 604/89 |
| 2009/0105660 | A1 * | 4/2009 | Muta | A61M 5/284 604/191 |
| 2012/0295221 | A1 * | 11/2012 | Cheetham | A61C 5/64 433/90 |
| 2013/0130197 | A1 * | 5/2013 | Jessop | B65D 25/082 433/90 |
| 2013/0226134 | A1 * | 8/2013 | Schabbach | A61M 5/2066 604/500 |
| 2014/0316342 | A1 * | 10/2014 | Kanazawa | A61M 5/284 604/191 |
| 2019/0038836 | A1 * | 2/2019 | Lumkemann | A61M 5/19 |

FOREIGN PATENT DOCUMENTS

| | | | | |
|---|---|---|---|---|
| JP | 09000628 | A * | 1/1997 | |
| JP | 09094602 | A * | 4/1997 | ............ B21B 1/163 |
| JP | 09-225032 | | 9/1997 | |
| JP | 09225032 | A * | 9/1997 | ............ A61M 5/284 |
| WO | WO 00/27316 | | 5/2000 | |
| WO | WO 00/45734 | | 8/2000 | |
| WO | WO 2005/039669 | | 5/2005 | |
| WO | WO 2007/046109 | | 4/2007 | |
| WO | WO 2008/094585 | | 8/2008 | |
| WO | WO 2009/104187 | | 8/2009 | |
| WO | WO 2015/036992 | | 3/2015 | |

OTHER PUBLICATIONS

International Preliminary Report on Patentability dated Mar. 24, 2016 From the International Bureau of WIPO Re. Application No. PCT/IL2014/050794.
International Search Report and the Written Opinion dated Apr. 14, 2015 From the International Searching Authority Re. Application No. PCT/IL2014/050794.
Communication Under Rule 164(2)(a) EPC dated Sep. 28, 2018 From the European Patent Office Re. Application No. 14777866.6 (4 Pages).
Office Action dated Jun. 16, 2019 From the Israel Patent Office Re. Application No. 244467 and Its Translation Into English. (5 Pages).
Communication Pursuant to Article 94(3) EPC dated Mar. 20, 2019 From the European Patent Office Re. Application No. 14777866.6 (4 Pages).

* cited by examiner

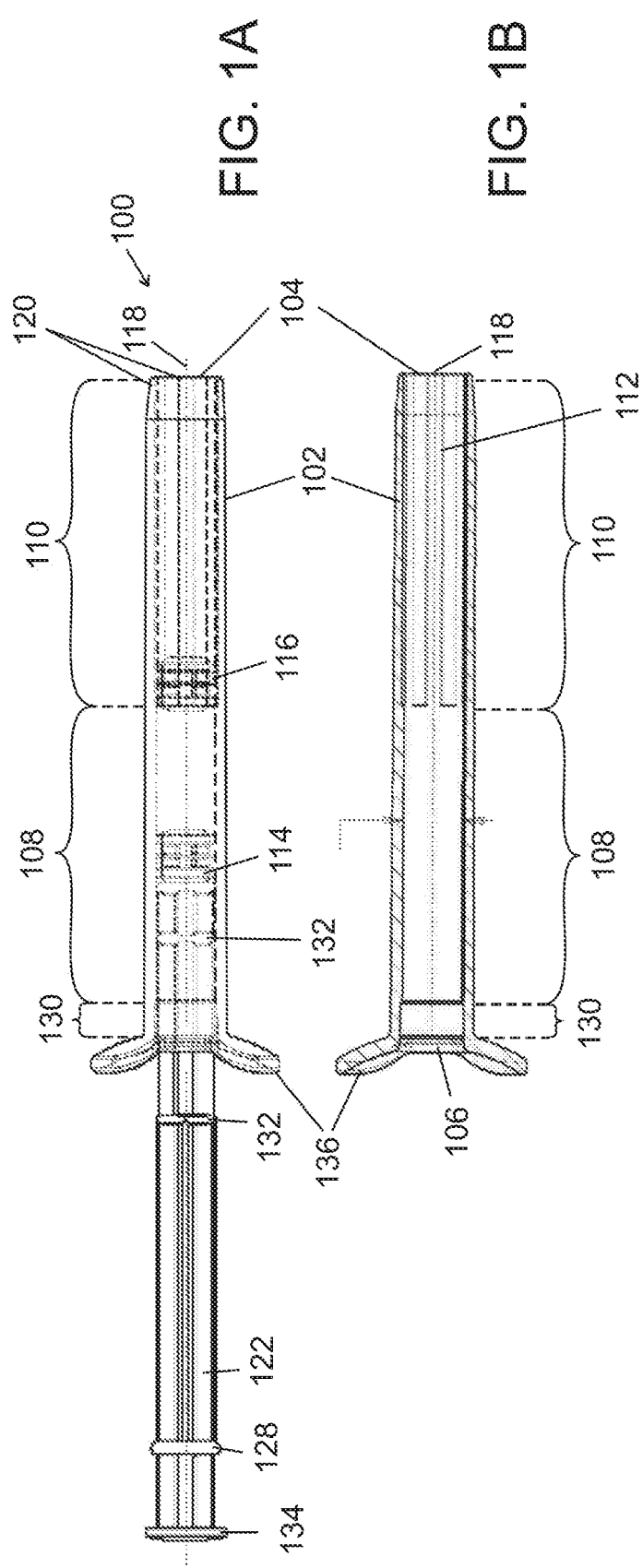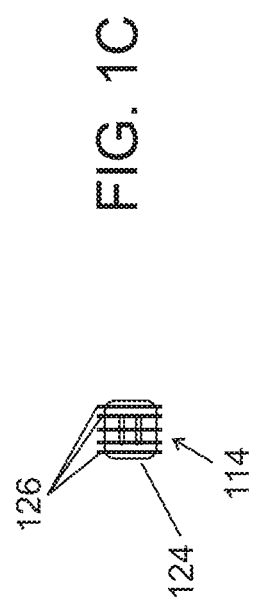

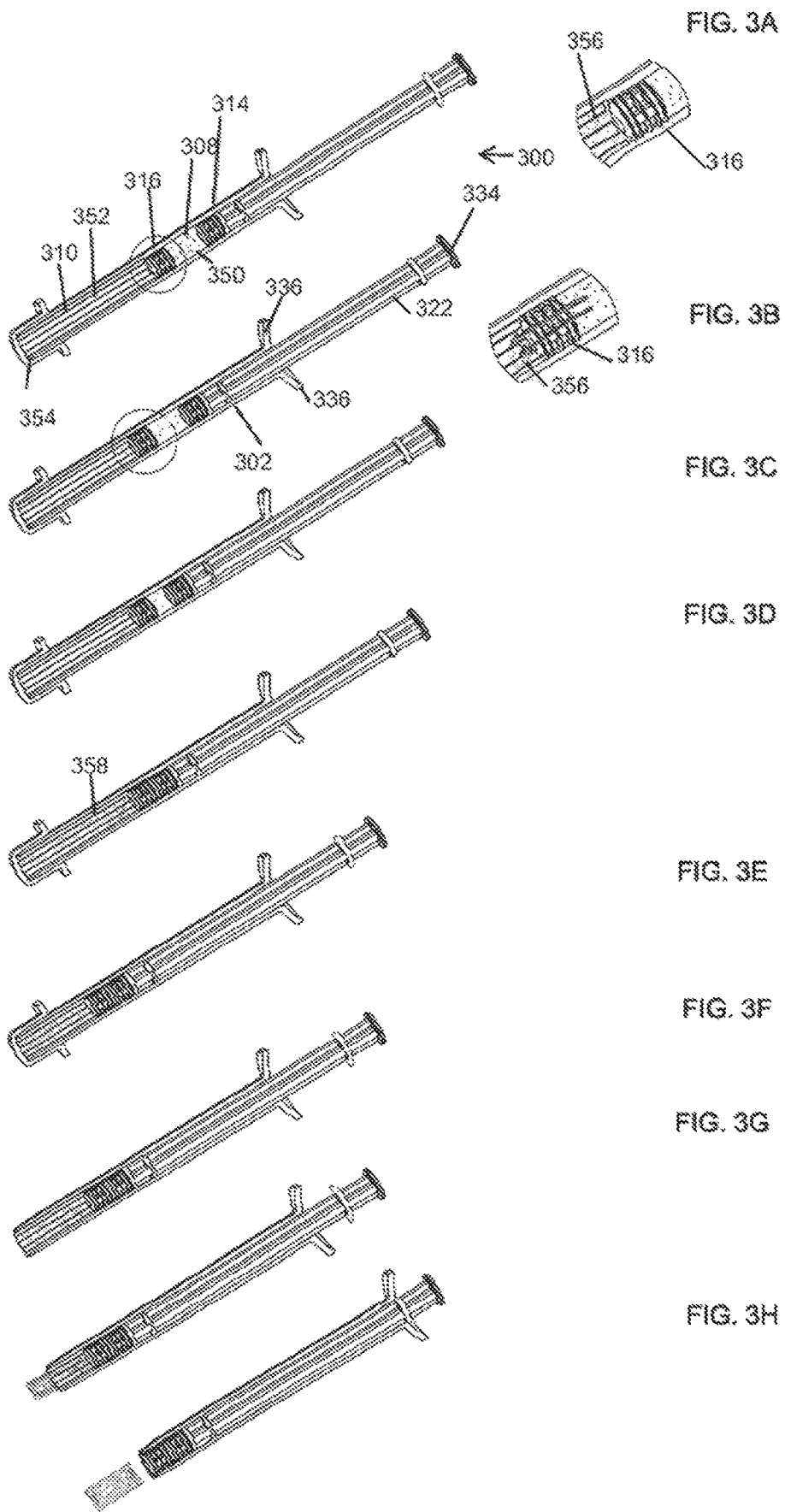

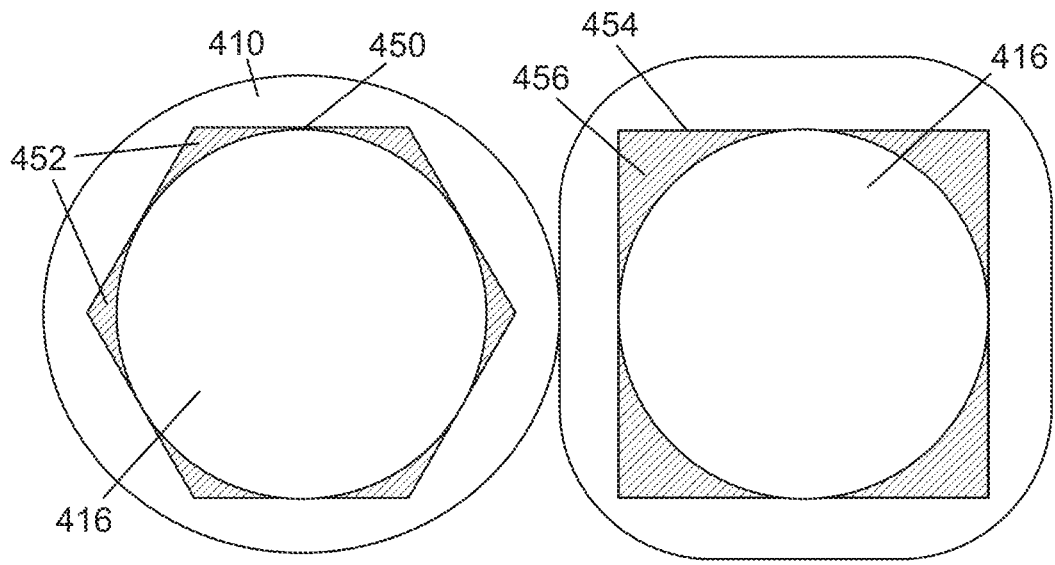
FIG. 4A
FIG. 4B
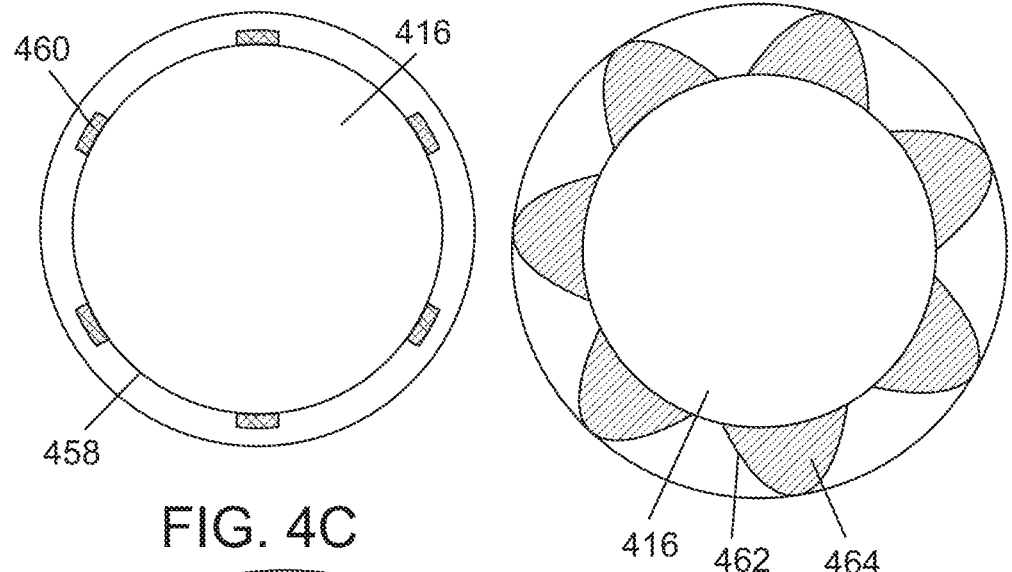
FIG. 4C
FIG. 4D
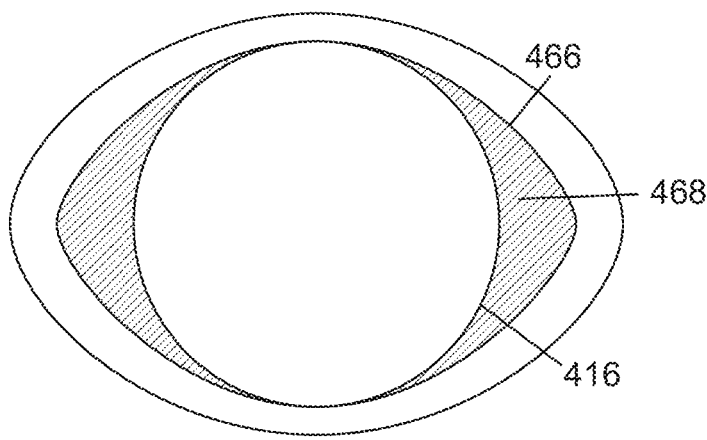
FIG. 4E

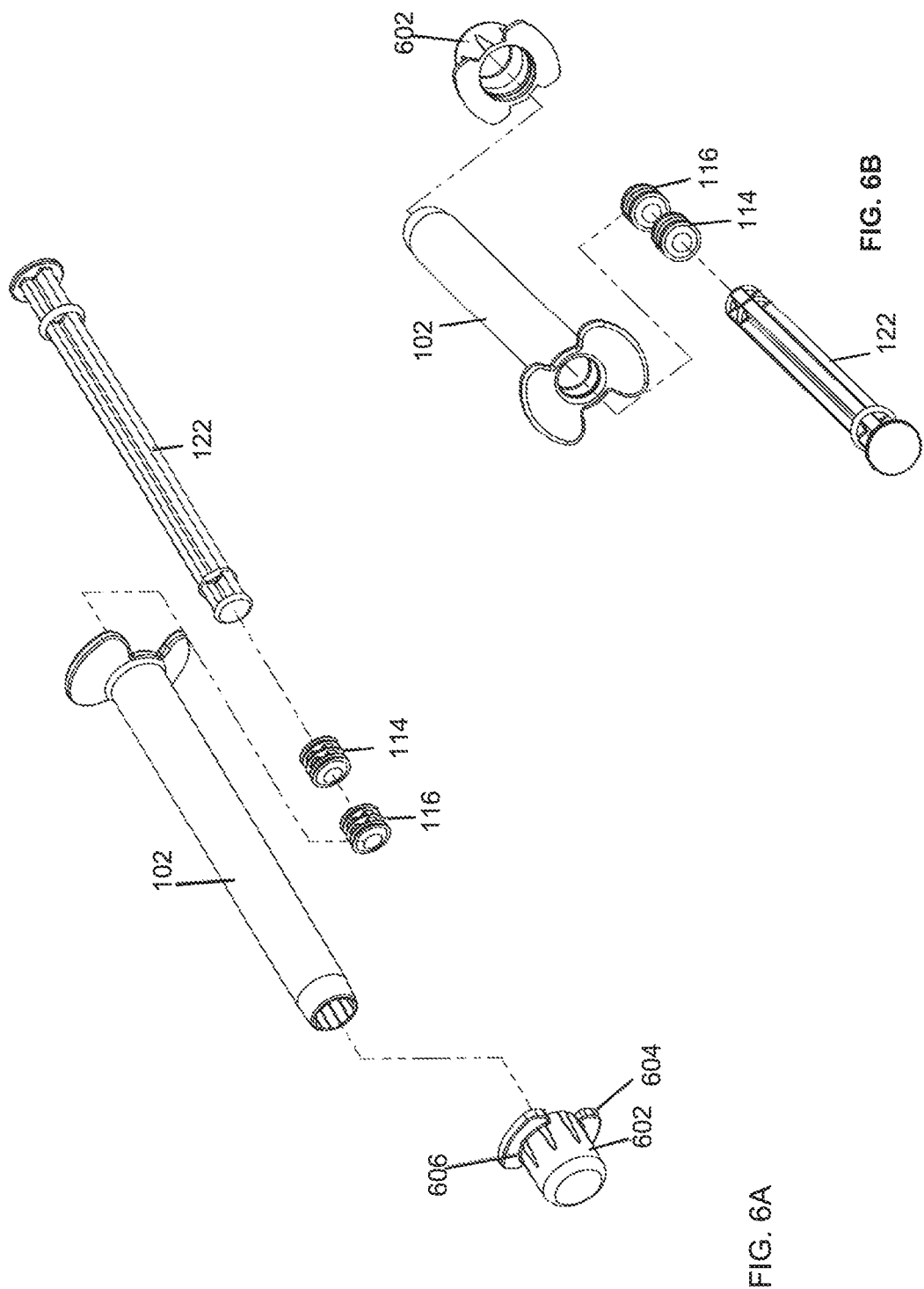

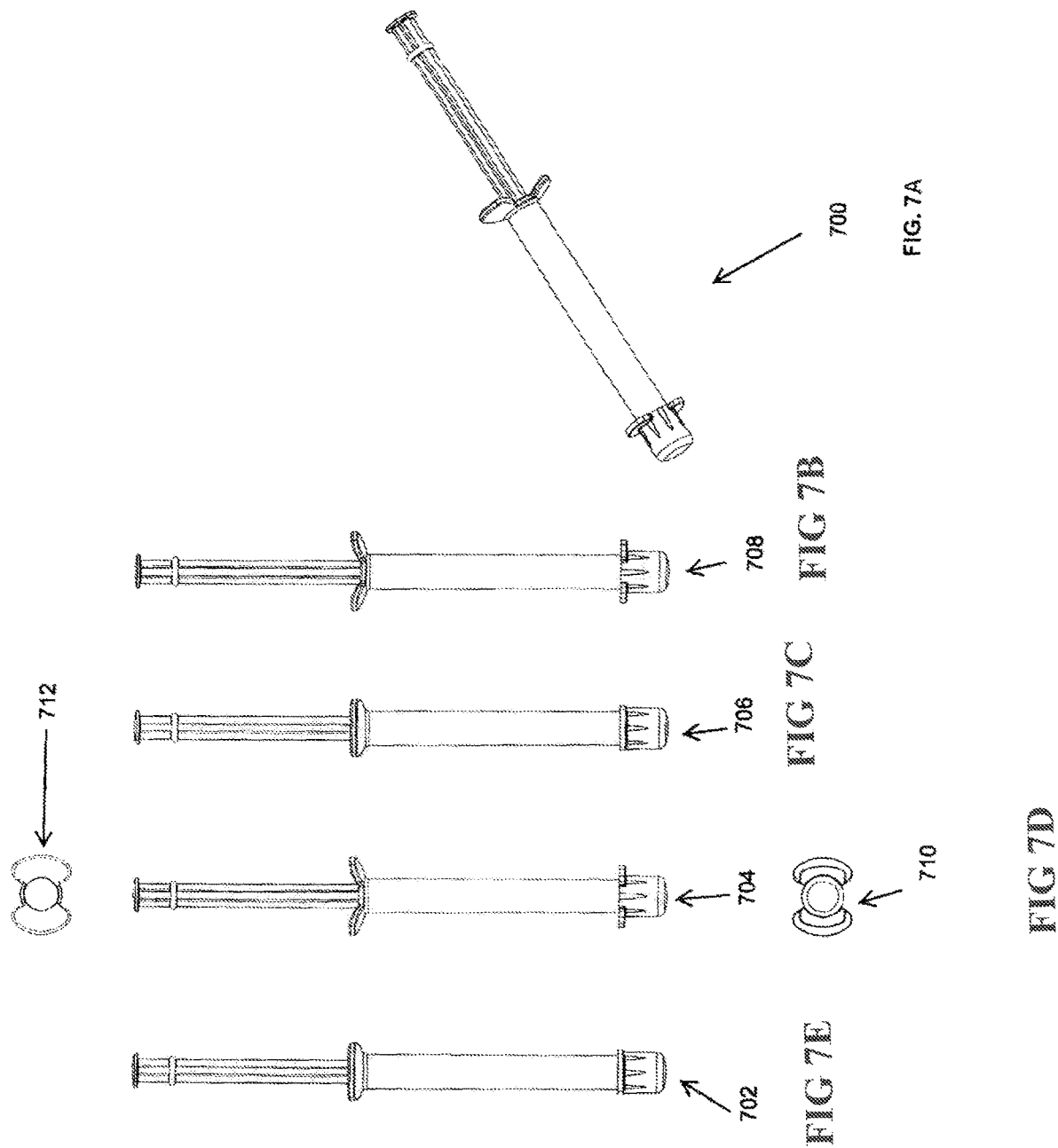

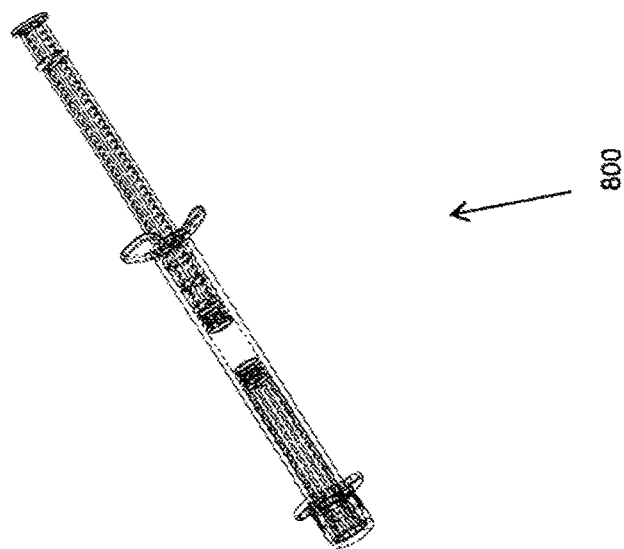
FIG. 8A
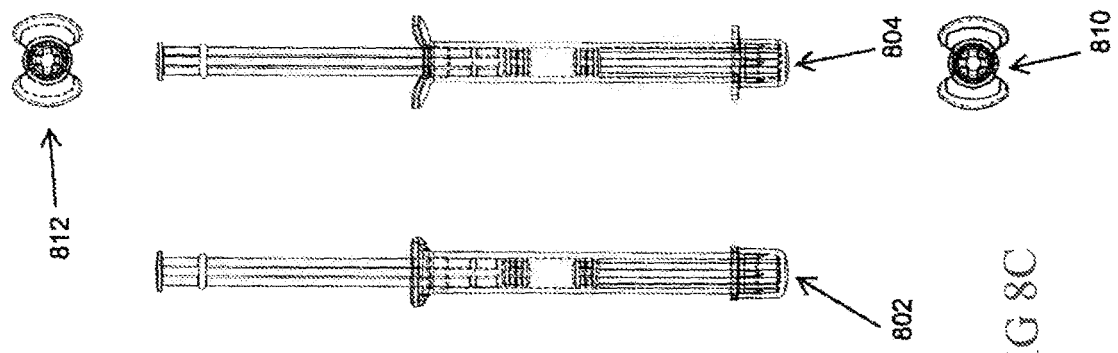
FIG. 8B
FIG. 8C

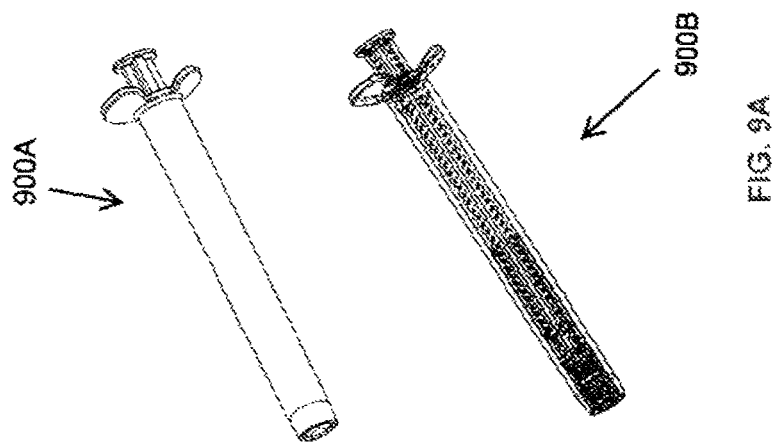
FIG. 9A
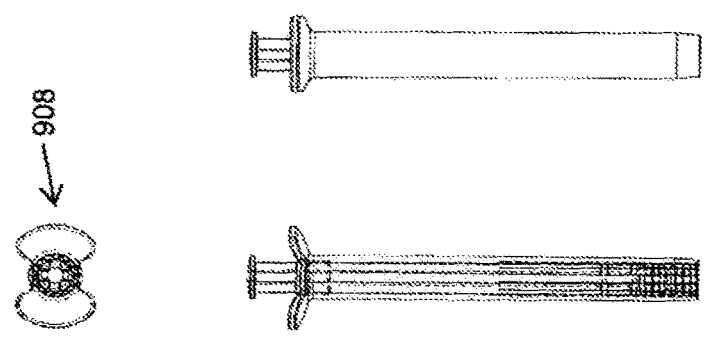
FIG 9B
FIG 9C
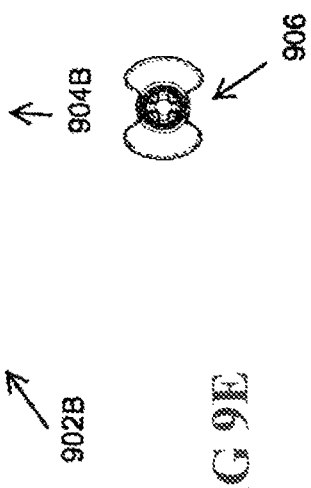
FIG 9D
FIG 9E

DUAL COMPONENT APPLICATOR

RELATED APPLICATIONS

This application is a National Phase of PCT Patent Application No. PCT/IL2014/050794 having International filing date of Sep. 4, 2014, which claims the benefit of priority under 35 USC § 119(e) of U.S. Provisional Patent Application No. 61/875,735 filed on Sep. 10, 2013. The contents of the above applications are all incorporated by reference as if fully set forth herein in their entirety.

FIELD AND BACKGROUND OF THE INVENTION

The present invention, in some embodiments thereof, relates to a dual component applicator and, more particularly, but not exclusively, to a dual component applicator for mixing substances to produce a cementitious substance.

A cementitious substance used to treat bones and/or teeth of a patient is produced by mixing a pre-cementitious substance in powder form with a liquid carrier. As the time from mixing to hardening of the cement is fairly short, the cement needs to be mixed right before the procedure takes place.

The cementitious substance is used to repair bone and/or teeth defects, for example, by bone implantation, bone augmentation, and/or as a bone graft. Defects may result from bone and joint operations such as, for example, orthopedics or maxillofacial surgery including surgical removal of cysts, foci of suppuration and malignant bone tumors. These medical procedures may result in voids, gaps and other bone defects. Other examples of bone defects include those resulting, for example, from compression fractures, high-energy trauma, peri-articular fractures, cranial-maxillo facial fractures, osteoporotic reinforcement (i.e. screw augmentation) and periodontal reconstruction.

Dentistry is an exemplary field in which repairing bone defects may be necessary optionally in addition to dental implants, for replacing missing teeth. When a person experiences teeth loss due to trauma or other circumstances, or suffers from periodontal disease, loss of interproximal crestal alveolar bone is one of the conditions which the practitioner may deal with. This bone loss may further result in the loss of a person's interproximal or papillary oral tissue between the corresponding teeth and may cause a bone defect that is very unappealing aesthetically, as well as difficult to restore. Without the proper regeneration of this bone defect, any replacement tooth is likely to be malpositioned, out of proportion, shape and form, and lack interproximal tissue for a natural appearance.

The cementitious material may also be used, for example, to provide osteogenic (bone forming), osteoconductive (providing an inert scaffold on which osseous tissue can regenerate bone), and/or osteoinductive (stimulating cells to undergo phenotypic conversion to osteoprogenitor cell types capable of formation of bone) properties.

The cementitious substance is shaped so as to fill the bone defect as desired. Shaping the cementitious substance may be achieved by hand or by means of a shaping tool such as a spatula, a spoon, a broad flat blade and the like.

The simplest way to mix the pre-cementitious substance and the liquid carrier is by manually mixing on a plate. However, the plate mixing method is extremely prone to contamination. Sterility is important, as the cement is inserted into the body of a patient. Furthermore, the plate mixing method is prone to error, as precise measurements of the pre-cementitious substance and the liquid are required to produce the correct cement.

Yahav, in International Patent Application Publication No. WO2009104187 discloses ". . . applicators for applying flowable mixtures formed by mixing a dry composition and a liquid carrier, which are particularly useful for preparing and applying bone graft compositions . . . " Yahav teaches an applicator preloaded with a predefined amount of the pre-cementitious material. When it is time to form the cement, the operator draws water into the applicator to activate the composition and form the cement. When the cement has been mixed enough, it is removed from the applicator. Use of the applicator requires training and experience by the operator; to ensure that the correct amount of fluid is drawn in, to judge how much to mix the substances, and how long to wait until the substance is ready for removal. Furthermore, keeping the liquid sterile until it is withdrawn into the applicator is problematic.

Szwarc, in U.S. Pat. No. 4,613,326 discloses a device for mixing a liquid carrier and a powder to form a liquid medicine for injection into a patient; "A two-component syringe assembly . . . . The barrel also includes a bypass defining a bypass zone positioned along the barrel for allowing fluid to flow around the bypass stopper when the bypass stopper is positioned intermediate the ends of the barrel in the bypass zone . . . . The barrier flange projects outwardly from the body portion into the space between the inside wall of the barrel and the outside of the body portion for acting as a barrier for blocking the path of fluid which may be propelled in a distal direction through the bypass when the syringe is being operated."

Szwarc attempts to solve the problem of maintaining sterility, by mixing the components within the syringe itself. The bypass zone allows the liquid to travel forward to mix with the powder. However, while injecting the medicine into a patient, medicine and blood are blown back towards the operator through the bypass zone. Therefore, on the one hand, the bypass zone needs to be made as small as possible to prevent the operator from being contaminated with the medicine and blood. On the other hand, the bypass zone should be made larger to ease the mixing process.

SUMMARY OF THE INVENTION

An aspect of some embodiments of the invention relates to a dual component applicator for mixing a fluid with a pre-cementitious material, and automatically removing excess fluid from the mixed cementitious material after the mixing. In exemplary embodiments, the cementitious material is removed through the distal opening of the applicator. The distal opening may be of continuous or substantially continuous cross section and hence not include a neck or restriction and thus is large enough to allow the removal of the mixed cementitious material simply by pushing, and without substantial deformation of the cementitious material due to having to squeeze through any kind of restriction.

In exemplary embodiments, there is a mismatch in shape between one or more valves and a distal portion of the internal wall of the applicator, forming the mixing mechanism. The mismatch allows water through, but does not allow the much larger cement particles to pass. Optionally, the mixing mechanism reaches the distal opening of the applicator.

According to an aspect of some embodiments of the present invention there is provided a mixing applicator for mixing a fluid substance with a solid substance to obtain a resulting substance having a desired consistency, the applicator comprising:

a hollow elongated barrel having distal and proximal openings, the elongated barrel having a first cross sectional shape along a first proximal portion of the elongated barrel defining a first chamber, and a different second cross sectional shape along a second distal portion of the elongated barrel defining a second chamber, the second cross sectional shape extending from the distal end of the first portion to the distal opening of the hollow elongated barrel;

a first and a second valve both slidably displaceable within the hollow elongated barrel and sequentially arranged along a longitudinal axis of the barrel, the first and second valves having a third cross-sectional shape being complementary to said first cross sectional shape, thereby providing fluid-tight engagement within said first cross-sectional shape, said third cross-sectional shape being mismatched with said second cross-sectional shape to form a mismatch zone along a length of said second chamber, said mismatch zone allowing fluid flow around the valves, thereby to allow said first and second valves to effect mixing of said fluid substance with said solid substance and subsequently to remove excess fluid to obtain said resulting substance having said desired consistency.

According to some embodiments of the invention, the third cross-sectional shape of both the first and second valves comprise a circular cross-sectional shape and the second cross-sectional shape of the second chamber comprises a hexagonal cross-sectional shape.

According to some embodiments of the invention, the second cross-sectional shape of the second chamber comprises a plurality of spaced apart elongated depressions arranged substantially coaxially to a longitudinal axis of the barrel.

According to some embodiments of the invention, the first and second valves contact the internal wall of the second chamber at least at 3 spaced apart areas.

According to some embodiments of the invention, the area of a spaced apart passage of the mismatch zone is about 1%-5% of the cross sectional area of the second chamber.

According to some embodiments of the invention, the first and second valves are sized and shaped for forming the fluid-tight engagement between the external perimeter of the valves and an internal wall of the first chamber, and for forming the mismatch zone between the external perimeter of the valves and an internal wall of the second chamber.

According to some embodiments of the invention, the fluid substance is a biocompatible fluid and the solid substance is a pre-cementitious material that forms a cementitious material upon mixing with the biocompatible fluid.

According to some embodiments of the invention, the solid substance is a bone graft composition comprising a plurality of particles of a pre-cementitious substance and a plurality of particles of a non-cementitious substance, wherein the plurality of particles of the non-cementitious substance is characterized by at least two non-overlapping ranges of particle size, the composition being characterized by a particle size distribution according to formula I:

$$T = a_0 S_0 + a_1 S_1 + a_2 S_2 + a_3 S_3 + a_4 S_4 + \ldots + a_i S_i + \ldots + a_n S_n \quad \text{formula I}$$

wherein:
T is the particle size distribution of the composition;
$S_0$ is a particle size range of the pre-cementitious substance;
$a_0$ is a percentage by weight of the particles of the pre-cementitious substance of the total weight of the composition;
i is an integer ranging from 1 to n;
$S_1, S_2, S_3, \ldots S_i$ are each a particle size range of the non-cementitious substance;
at least two of the $S_1, S_2, S_3, \ldots S_i$ are non-overlapping particle size ranges;
$a_1, a_2, a_3, \ldots a_i$ are each a percentage by weight of the particles of the non-cementitious substance having the $S_1, S_2, S_3, \ldots S_i$ particle size range of the total weight of the composition, the pre-cementitious substance and the non-cementitious substance being selected such that upon contacting a mixture of both the substances with an aqueous solution, a biocompatible cementitious material is formed.

According to some embodiments of the invention, the fit between the third-cross sectional shape and the second cross-sectional shape in the mismatch zone is sufficient for the valves to seal against the solid and the resulting substance.

According to some embodiments of the invention, the length of the internal wall of the second chamber when measured along a longitudinal axis of the barrel is longer than the combined lengths of the first and second valves.

According to some embodiments of the invention, the distal opening of the hollow elongated barrel has a fourth cross-sectional shape that is substantially the same as the second cross-sectional shape of the second chamber.

According to some embodiments of the invention, the barrel is made out of a transparent material.

According to some embodiments of the invention, the first and second valves are made out of a material that is resistant to sterilization methods. Optionally, the material is plastic.

According to some embodiments of the invention, the applicator further comprises a rod in mechanical communication with the first valve so that displacement towards the distal end of the rod distally displaces the first valve, the second valve being distally displaced by mechanical contact exerted by the first valve.

According to some embodiments of the invention, the fourth cross-sectional shape of the distal opening is too large for direct injection of the resulting substance for use inside a body of a patient.

According to some embodiments of the invention, the fourth cross-sectional shape of the distal opening is too large for attachment to a needle used to inject substances into the body.

According to some embodiments of the invention, the applicator further comprises a cap having an internal cross sectional size and shape to seal the distal opening.

According to an aspect of some embodiments of the present invention there is provided a mixing applicator for mixing a biocompatible fluid with a solid pre-cementitious substance to obtain a resulting cementitious substance having a desired consistency, the applicator comprising:

a hollow elongated barrel having distal and proximal openings, the elongated barrel having a first cross sectional shape along a first proximal portion of the elongated barrel defining a first chamber, and a different second cross sectional shape along a second distal portion of the elongated barrel defining a second chamber, the first chamber being pre-loaded with the biocompatible fluid and the second chamber being pre-loaded with the pre-cementitious substance that forms the cementitious substance when mixed with the biocompatible fluid;

a first valve and a second valve, both slidably displaceable within the hollow elongated barrel and sequentially arranged along a longitudinal axis of the barrel, the first and second valves having a third cross-sectional shape being complementary to said first cross sectional shape, thereby providing fluid-tight engagement within said first cross-sectional shape, said third cross-sectional shape being mismatched with said second cross-sectional shape to form a mismatch zone along a length of said second chamber, said mismatch zone allowing biocompatible fluid flow around the valves, thereby to allow said first and second valves to effect mixing of said biocompatible fluid with said pre-cementitious substance and subsequently to remove excess biocompatible fluid to obtain said resulting cementitious substance having said desired consistency;

a cap disposed on the distal opening of the hollow elongated barrel to seal the distal opening; and a rod in mechanical communication with the first valve so that distal displacement of the rod distally displaces the first valve, the second valve being distally displaced by mechanical forces exerted by the first valve;

wherein the first valve and the second valve are arranged so that displacement in the distal direction of the rod forces the biocompatible fluid through the mismatch zone to mix with the pre-cementitious substance, and additional distal displacement of the rod forces a fly-back of excess biocompatible fluid out of the cementitious substance through the mismatch zone, to obtain said resulting cementitious substance having said desired consistency.

According to some embodiments of the invention, the length of the internal wall of the second chamber when measured along a longitudinal axis of the barrel is longer than the combined lengths of the first and second valves.

According to an aspect of some embodiments of the present invention there is provided a method of mixing a biocompatible fluid and a pre-cementitious substance to form a cementitious substance having a desired consistency suitable for bone or teeth treatment, the method comprising:

allowing flow of a biocompatible fluid through a mismatch zone, so that the biocompatible fluid mixes with a pre-cementitious substance to form a cementitious substance;

compressing the cementitious substance; and allowing excess fluid to fly-back through the mismatch zone, so that retained cementitious material has the desired consistency.

According to some embodiments of the invention, the amount of biocompatible fluid is more than is required to produce the cementitious material. Optionally, most of the excess fluid is removed during the compression.

According to some embodiments of the invention, mixing the fluid with the pre-cementitious material is performed in any direction relative to the force of gravity.

According to some embodiments of the invention, mixing the fluid with the pre-cementitious material is performed by applying continuous manual pressure in a distal direction.

According to some embodiments of the invention, the method further comprises exposing the cementitious material to an external environment. Optionally, the method further comprises removing the cementitious material into the external environment without substantially deforming the cementitious material.

According to some embodiments of the invention, the mixing is performed by gently applied manual finger pressure.

According to some embodiments of the invention, the method further comprises repairing bone or teeth using the cementitious material.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1A is a side view of a dual component applicator for mixing two substances, in accordance with exemplary embodiments of the invention;

FIG. 1B is a side view of a hollow elongated barrel of the applicator of FIG. 1A;

FIG. 1C is a side view of the valve of FIG. 1A;

FIGS. 3A-3H are visual representations corresponding to the mixing method of FIG. 2, in accordance with exemplary embodiments of the invention;

FIGS. 4A-4E are cross sectional views of the applicator to illustrate some exemplary mismatch zones;

FIGS. 6A-6B are elevated views showing the arrangement of the components of the applicator of FIG. 1A, in accordance with exemplary embodiments of the invention;

FIGS. 7A-7E are schematic illustrations of various views of the pre-loaded applicator, in accordance with exemplary embodiments of the invention;

FIGS. 8A-8C are a schematic illustrations corresponding to FIG. 7; and

FIGS. 9A-9E are schematic illustrations of various views of the applicator after completion of the mixing process, in accordance with exemplary embodiments of the invention.

DESCRIPTION OF SPECIFIC EMBODIMENTS OF THE INVENTION

Figure 2:
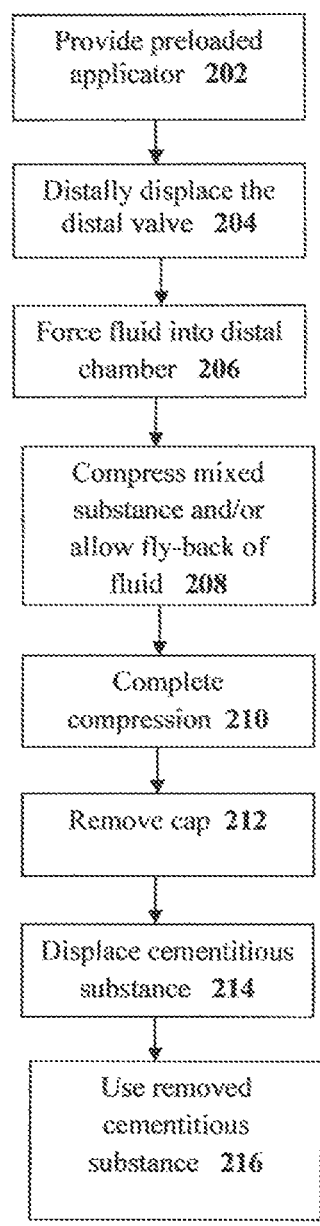
FIG. 2 is a method of mixing using a dual component applicator, in accordance with exemplary embodiments of the invention.

An aspect of some embodiments of the invention relates to a pre-loaded dual component applicator for mixing a fluid (in a first chamber) with a pre-cementitious substance (in a second chamber) to form a cementitious substance, the applicator having a fluid exchange region along the entire length of the second chamber until a distal opening of the applicator. In exemplary embodiments, excess fluid is automatically removed during compression of the mixed cementitious substance. Optionally, the mixing is performed with the applicator sealed until the cementitious material is ready for removal. Advantageously, the mixing may be performed without prior training, without needing to measure precise amounts of fluid and/or in a manner that prevents or reduces leaks.

As used herein, the term "proximal" means closer to the user holding the applicator.

As used herein, the term "distal" means further away from the user holding the applicator.

In exemplary embodiments, there is a mismatch between a valve within the second chamber and the inner walls of the second chamber, which provides a mixing mechanism within the fluid exchange region, as fluid may pass through the gap brought about by the mismatch, but the cement particles cannot. As used herein, the term "fly-back" means in a distal to proximal direction.

In exemplary embodiments, the mismatch region is large enough to allow excess fluid to fly-back to the first chamber and/or to the proximal portion of the applicator. In exemplary embodiments, the mismatch region is small enough to prevent fly-back of the mixed cementitious material.

In exemplary embodiments, excess fluid is flown-back through the mismatch region during compression of the mixed cementitious substance. Optionally, when the compression is completed, the mixed cementitious substance contains the correct amount of fluid, with the excess fluid having been removed by the fly-back.

An aspect of some embodiments of the invention relates to a pre-loaded dual component applicator for mixing a fluid (in a first chamber) with a pre-cementitious substance (in a second chamber) to form a cementitious substance, the applicator having a distal opening for releasing the cementitious substance that is unsuitable for injection.

Optionally, the distal opening of the applicator is too large for injection through tissue such as skin, bone and/or muscle and/or unsuitable for direct injection into a bone cavity. Alternatively or additionally, the distal opening is unsuitable for attachment of a needle, for example, too large to allow attachment of the needle.

In exemplary embodiments, the internal size and/or shape of the distal opening is substantially the same as the cross sectional size and/or shape of the second chamber housing the cementitious substance. The distal opening may be of constant or substantially constant cross-section and thus not include a neck or substantial restriction. For example, the distal opening is at least about 70%, or about 80%, or about 90% of a cross sectional dimension (e.g., diameter) of the inner walls of the second chamber.

Optionally, the size and/or shape of the distal opening is large enough so that the cementitious material is released without substantial deformation of the cementitious material occurring during release, for example, a change in cross sectional dimension of no more than about 10%, or about 20%, or about 30%. Optionally, the distal opening is large enough so that the cementitious material is released without having to apply a pressure strong enough to deform the cementitious material.

In exemplary embodiments, the applicator is preloaded with a suitably sized cap for sealing the distal opening. Optionally, the sealing is hermetic.

In exemplary embodiments, the cementitious material is unsuitable for injection and/or would not flow through a needle or other similarly sized opening. For example, pressure that would break the applicator would need to be applied to the cementitious material to make it flow through the needle.

An aspect of some embodiments of the invention relates to a dual chamber applicator that is sealed (e.g., hermetically), pre-loaded with a biocompatible fluid in a first chamber and a pre-cementitious material in a second chamber, and has an internal mixing mechanism so that mixing of the fluid with the pre-cementitious chamber occurs inside the applicator without breaking the seal. Optionally, the formed cementitious material is suitable for bone treatment, for example, bone repair.

In exemplary embodiments, the outer surface of a barrel of the applicator (housing the chambers) is flush. For example, the mixing components and the mixing mechanism are stored within the barrel, without protruding above the level exterior surface.

In exemplary embodiments, a cap seals the distal opening of the applicator.

Optionally, the cap is only removed after the cementitious substance has been formed by mixing.

An aspect of some embodiments of the invention relates to a method of using an optionally pre-loaded and optionally sealed dual chamber applicator to mix a biocompatible fluid with a cementitious material to produce a cementitious material by removing excess fluid from the mixture. Optionally, the cementitious material is used to treat bones.

In exemplary embodiments, the method comprises allowing fluid to flow from a first chamber, to a second chamber housing the pre-cementitious material, the fluid flowing through a mismatch region. In exemplary embodiments, the fluid displaces air in the second chamber, the air being blown-back into the first chamber. The method further comprises compressing the mixed substance between a valve in the second chamber and a cap at the distal end of the applicator, wherein excess fluid is flown-back from the second chamber during the compressing. The method further comprises removing the sealing cap to remove the formed cementitious material. Optionally, the cementitious material is removed without substantial deformation in shape and/or in one piece, for example, without being stretched out and/or in multiple pieces.

In exemplary embodiments, the method is performed by distal displacement, for example, by pushing a rod having a valve at the distal end thereof. Optionally, the distal displacement is continuous. Optionally, some rest periods are allowed during the distal movement. Optionally, there is no proximal displacement. For example, back and forth motion of the rod is not required.

The present invention, in some embodiments thereof, relates to a dual component applicator and, more particularly, but not exclusively, to a dual component applicator for mixing substances to produce a cementitious substance.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Overview of Applicator

Referring now to the drawings, FIG. 1A is a side view of a dual component applicator 100 for mixing two substances, in accordance with exemplary embodiments of the invention. FIG. 1B is a side view of a hollow elongated barrel 102 of applicator 100 of FIG. 1A. In exemplary embodiments, the first substance is a biocompatible fluid that is mixed with a pre-cementitious second substance to form a cementitious substance. For clarity, the fluid and pre-cementitious substance are not shown in FIGS. 1A-1B. Advantageously, applicator 100 may allow for the mixing in a failsafe manner, without requiring previous training, without external contamination, without spills and/or without needing to measure specific amounts of the fluid and/or pre-cementitious substance.

In exemplary embodiments, applicator 100 comprises hollow elongated barrel 102 having a distal opening 104 and a proximal opening 106.

In exemplary embodiments, applicator 100 comprises a first valve 114 and a second valve 116 slidably displaceable within barrel 102. First valve 114 and second valve 116 are sequentially arranged along a longitudinal axis 118 of barrel 102, for example, valve 114 is proximal to valve 116.

Barrel 102 is divided into at least two regions which define at least two chambers. A first chamber 108 is defined by a first cross sectional shape along a proximal portion of barrel 102. A second chamber 110 is defined by a second cross sectional shape along a distal portion of barrel 102. As will be described in greater detail below, the cross sectional shapes of chamber 108 and chamber 110 are different. For example, chamber 108 is a circle in cross section, and chamber 110 is a hexagon (shown as lines 112) in cross section, where the hexagon of chamber 110 is larger than the circle of chamber 108, so that when seen in cross section (e.g., from distal end 104), the circle appears to be inscribed within the hexagon.

In exemplary embodiments, valves 114 and 116 are sized and shaped for fluid-tight engagement when located inside chamber 108, for example, valves 114 and/or 116 have a diameter substantially the same as the internal diameter of chamber 108. When valves 114 and/or 116 are inside chamber 110, a mismatch zone is formed between the external perimeter of valves 114 and/or 116 and the internal wall of chamber 110. The mismatch zone allows fluid to flow between chambers 108 and 110, that is in either direction. The mismatch zone may comprise of several spaced apart openings. For example, the mismatch zone is formed by spaces between circular valve 114 and/or 116 circumscribed within hexagonally shaped chamber 110. The mismatch zone may also comprise both the mismatch zone formed by valve 114 and the mismatch zone formed by valve 116.

Optionally, in use, and as will be described in more detail below, applicator 100 is preloaded. Optionally, a biocompatible fluid is housed in chamber 108, between valves 114 and 116. Optionally, a pre-cementitious substance is housed in chamber 110, between valve 116 and distal end 104 (which optionally is sealed with a cap). As will be described in greater detail below, the fluid from chamber 108 enters chamber 110 through mismatch zone 120, forming the cementitious substance in chamber 110. Excess fluid from the cementitious substance is flowed-back through mismatch zone 120 to leave the cementitious substance at the intended consistency for use. The formed cementitious substance is removed through distal opening 104.

In exemplary embodiments, chamber 110 is longer than the total combined length of valves 114 and 116, as measured along longitudinal axis 118, for example, at least about 10% longer, or at least about 50% longer, or at least about 100% longer, or other smaller, intermediate or larger percentages. Optionally, the length of chamber 110 is about 10 mm, or about 20 mm, or about 30 mm, or about 50 mm, or other smaller, intermediate or larger lengths. Advantageously, the length of chamber 110 forms the mismatch zone along both valves 114 and 116, allowing fluid flow past both valves, for example, when both valves are in end to end contact.

Optionally, the inner cross sectional shape of chamber 110 extends to distal opening 104. Alternatively or additionally, mismatch zone 120 extends to distal opening 104. Alternatively, the inner cross sectional shape of chamber 110 extends close to distal opening 104, for example, within about 1 mm, or about 3 mm, or about 5 mm, or about 7 mm, or other smaller, intermediate or larger dimensions.

Optionally, the inner cross sectional shape of chamber 110 extends from the distal end of chamber 108, for example, there is an abrupt change in shape at the boundary.

Optionally, the inner cross sectional size and shape of distal opening 104 is the same as the inner cross sectional size and shape of chamber 110. Advantageously, the cementitious material formed within chamber 110 may be easily removed, for example, intact and/or without significant deformations through opening 104. Alternatively, there is some tapering of the inner walls of chamber 110 at distal opening 104, for example, the diameter is reduced by about 5%, or about 10% or about 20%, or other smaller intermediate or larger percentages, or the diameter is reduced to substantially match the internal diameter of chamber 108. Alternatively or additionally, there is a change in shape of the cross section of distal opening 104, for example, the shape is substantially similar to the cross sectional shape of chamber 108. Optionally, opening 104 is sized and/or shaped to retain valves 114 and/or 116 inside barrel 102. Advantageously, valves 114 and/or 116 are prevented from exiting barrel 102 through opening 104, and entering the anatomical treatment site during device operation.

Optionally, the combined total length of pushrod 122, valve 114 and 116 is less than or equal to the length of barrel 102. Alternatively, the location of flange 128 is selected so that the length of pushrod 122 that is able to enter barrel 102 combined with the lengths of valves 114 and 116 is less than or equal to the length of barrel 102.

Optionally, distally displacing pushrod 122 as deeply as possible into barrel 102 will not push valve 116 and/or valve 114 out of barrel 102. Advantageously, the applicator may be operated without fear of valve 116 and/or valve 114 escaping from barrel 102 into the patient's anatomical treatment site.

FIG. 1C is a side view of valve 114 (or 116) of FIG. 1A, valve 114 being shown in isolation from applicator 100. Optionally, valve 114 is made out of a solid core 124 with a number of radial extensions 126. Extensions 126 have a cross sectional size and shape to provide a fluid-tight seal when valve 104 is inside chamber 108. Optionally, each extension 126 has a relatively short length (e.g., when compared to total length of valve 114) when measured along longitudinal axis 118. Advantageously, extensions 126 may provide a fluid tight seal while also reducing friction with the internal walls of barrel 102 so that valve 114 may be distally displaced with pressure that is low enough to prevent damage to applicator 100. Alternatively, valve 114 is only made out of a suitably sized and shape core 124 without extensions 126.

Optionally, valves 114 and/or 116 are made out of a material that is resistant to sterilization methods, for example, heat and/or radiation, gas. Some not necessarily limiting examples of the material include; glass, plastic and/or polymers, for example, polyethylene and/or polypropylene. Advantageously, applicator 100 may be preloaded, sealed and then the internal contents are sterilized, which may provide for a simpler technique and/or lower sterilization costs.

Optionally, valve 114 and/or 116 are made out of a material that does not deform under pressures experienced during standard mixing operations, for example, plastic. Advantageously, the non-deformable material maintains the patency of the mismatch zones, even during pressures applied to valves 114 and/or 116 during the mixing procedure.

Optionally, applicator comprises pushrod 122, inserted through proximal opening 106 of barrel 102. Optionally, a proximal region 130 of barrel 102 has a cross sectional size and/or shape larger than channel 108, for example, to make it easier to insert pushrod 122 into barrel 102. Pushrod 122 mechanically engages valve 114, for example, by temporary contact, or by being attached with glue, screw and thread or other attachment methods.

Optionally, pushrod 122 comprises a flange 128 in near proximity to a proximal end thereof. Optionally, flange 128 has a larger shape and/or diameter than proximal opening 106. Advantageously, the insertion depth of pushrod 122 into barrel 102 is selected by the location of flange 128 along the length of pushrod 122.

Optionally, pushrod 122 comprises one or more radial extensions 132 in near proximity to a distal end thereof. Optionally, the extensions 132 are sized and/or shaped to be in fluid tight contact with inner walls of chamber 108. Advantageously, extensions 132 may help to keep contents of applicator 100 hermetically sealed.

Pushrod 122 is distally displaced by a user pushing against an optional flange 134 located on the proximal end of pushrod 122. Optionally, barrel 102 is held in place, for example, by the user grabbing flanges 136 on the proximal end of barrel 102.

Optionally, one or more components of applicator 100 (e.g., barrel 102, valve 114, valve 116, pushrod 122 and/or a cap for opening 104) are transparent, for example, to allow visualization of the fluid, pre-cementitious substance and mixed cementitious substance. In one example, the material is a clear plastic. Alternatively, the one or more components are non-transparent, for example, to allow long term storage of substances that break down under light. Advantageously, the applicator may be used blindly, without having to see any internal structures or substances.

Advantageously, the applicator may be manufactured using low cost methods for example, injection molding.

Advantageously, the applicator may be disposable.

Method

FIG. 2 is a method of mixing a fluid and a pre-cementitious substance to form a cementitious substance, in accordance with exemplary embodiments of the invention. Reference will be made to FIGS. 3A-3H, which are visual representations corresponding to boxes of the method.

Advantageously, the method is fail safe, as the method may be performed without prior training, and/or without special preparations, for example, without having to preload a specific amount of fluid.

Optionally, the mixing method is performed while holding the applicator in any orientation relative to gravity. For example, no specific orientation is required to force air out.

Optionally, the mixing method is performed only with displacement of the valve towards the distal end, and no back and forth motion of the valves is required and/or no additional agitation is required for the mixing. Optionally, continuous displacement towards the distal end, using the pushrod, produces the cementitious substance.

Optionally, the mixing method is performed without requiring the user to exert strong pressures. Optionally, the mixing method is performed by the application of manual pressure. Optionally, the manual pressure is applied by one finger, for example, the thumb. Optionally, the manual pressure is applied gently, for example, by the user pushing with the finger without experiencing strain or pain of the finger.

Optionally, the mixing method is performed without a pressure buildup within the applicator. Optionally, the pressure within the applicator is maintained at about atmospheric pressure. Any pressure applied within the applicator causes an almost immediate displacement of an internal component and/or substance, thereby releasing the pressure and preventing or reducing pressure buildup.

Optionally, a resistance to the gently applied manual pressure (e.g., pain and/or strain to the finger) is an indication to the operator that there is a problem within the applicator. For example, that the pre-cementitious substance has been contaminated with liquid and hardened. Advantageously, upon experiencing the resistance, the user does not need to continue applying stronger pressures or investigate the problem. The user may simply discard the applicator and try with a new applicator.

Advantageously, the pressure may be kept low enough to prevent damage to components and/or materials within applicator 300. Advantageously, the low pressures within the applicator prevent squirting and/or leaks of the fluid and/or substances therein. Such squirts or leaks are unwanted, as contamination of the operator and/or applicator may result.

Optionally, the mixing method is performed without precisely timing the mixing process.

Optionally, at 202, and as shown in FIG. 3A, a preloaded applicator 300 is provided, for example, the applicator as described with reference to FIGS. 1A-1B. In exemplary embodiments, a proximal chamber 308 (chamber 108 in FIGS. 1A and 1B) is preloaded with a biocompatible fluid 350, and a distal chamber 310 is preloaded with a pre-cementitious substance 352. Fluid 350 is contained between proximal valve 314 and distal valve 316. Pre-cementitious substance 352 is contained between distal valve 316 and a distal cap 354.

Optionally, the amount of fluid 350 is in excess of the amount required to mix with pre-cementitious substance 352, for example, about 10%-100% more, or about 20%-70% more, or about 30%-60% more, or about 20%, or about 30%, or about 50% more, or other smaller, intermediate or larger percentages or ranges.

As shown in the blow-up box, valve 316 lies in a fluid-tight position within chamber 308, in close proximity to an inner wall of chamber 310, for example, a hexagonal shaped cross section 356. Alternatively, valve 316 is disposed further away from chamber 310. The position may be selected, for example, according to the risk of valve 316 moving into chamber 310 and causing a premature fluid leak during shipping.

Optionally, in addition to the pre-cementitious substance, the distal and/or proximal chambers contain other non-cementitious substances. Optionally, the pre-cementitious substance comprises one or more different types of substances.

Optionally, the pre-cementitious substance is in the form of a dry powder.

Optionally, the pre-cementitious substance is porous.

Optionally, the cementitious substance and optionally the non-cementitious substance are selected such that upon contacting a mixture thereof with an aqueous solution, a biocompatible cementitious substance is formed.

Not necessarily limiting examples of the fluid include, an aqueous solution, water, purified water, medical grade water for injection or saline (0.9% NaCl in water, typically purified and sterile). Such biocompatible solutions may afford biocompatible cementitious substances.

As used herein, the term "biocompatible" refers to a material, substance, cementitious material or composition, which is substantially non-toxic, does not cause severe adverse biological effect, or lethality in an animal when administered to a subject at pharmaceutically acceptable amounts, doses and/or rates.

At 204, and as shown in FIG. 3B (more clearly in the blow-up), valve 316 is distally displaced into chamber 310, so that the entire length of valve 316 lies within hexagon shaped section 356. Fluid 350 flows (shown by the arrows in the blow-up) from chamber 308 into chamber 310 through the mismatch zone formed between valve 316 and hexagon 356.

The distal displacement of valve 316 and the pressured exerted on fluid 350 is created by a user (e.g., human) distally displacing pushrod 322 into barrel 302 by applying pressure to the proximal end of pushrod 322. For example, the thumb of the user presses against an optional proximal flange 334 of pushrod 322, while the index finger and middle finger provide support and/or counter pressure by optional proximal flanges 336 on the proximal end of barrel 302. Pushrod 302 is in mechanical communication with valve 314. Distally displacing valve 314 exerts pressure on fluid 350, which then forces valve 316 distally until the position in chamber 310, as shown in the blow-up. As fluid 350 does not significantly compress under the applied pressure, the distance between valves 314 and 316 is maintained during the distal displacement, until valve 316 reaches chamber 310.

At 206, and as shown in FIG. 3C, additional fluid 350 flows from chamber 308 into chamber 310. Optionally, pressure exerted by pushrod 322 that is transferred to fluid 350 causes fluid 350 to flow through the mismatch zone into chamber 352.

Optionally, the pressure does not cause significant displacement of valve 316, for example, the friction between valve 316 and walls of chamber 310 is enough to resist the force and/or the mismatch zone is large enough to accommodate the fluid of fluid 350 therethrough. Optionally, as shown, the pressure reduces the amount of fluid 350 within chamber 308 by distally displacing valve 314 without significantly distally displacing valve 316.

Optionally, fluid 350 flowing into chamber 310 displaces air within chamber 310. Optionally, the air flies back through the mismatch zone, for example, into chamber 308. Advantageously, air already present within pre-cementitious substance 352 may help the mixing, by allowing fluid 350 to enter within substance 352.

At 208, and as shown in FIG. 3D, pressure is applied until valve 314 contacts valve 316. Optionally, additional exerted pressure compresses the mixed cementitious material 358.

Optionally, additional distal pressure is applied, distally displacing valve 314 from a fluid tight position within chamber 308 into chamber 310. Another mismatch zone is formed between valve 314 and walls of chamber 310.

At 210, and as shown in FIG. 3E, both valves 314 and 316 are in chamber 310, forming an elongated mismatch zone between both valves 314 and 316 and walls of chamber 310. Optionally, as valves 314 and 316 are distally displaced (e.g., by the exerted pressure) substance 358 is further compressed. The compression pushes out excess fluid from substance 358, for example, most of the excess fluid, or about 50%-90%, or about 60%-80% of the excess fluid. The excess fluid is allowed excess fluid to fly-back through the mismatch zone of valves 314 and 316.

Optionally, a predefined mark is disposed (e.g., painted, scratched) on the outer barrel at the distal chamber 310. The predefined mark may aid the user in determining the amount of force to apply to pushrod 322 when compressing cementitious substance 358. The user may distally displace pushrod 322 until the distal end of valve 316 reaches the predefined mark. The location of the predefined mark may be selected according to the desired viscosity of the cementitious material 358. A predefined mark closer to the distal end of the applicator may produce cementitious material 358 that is more viscous due to more fluid removal. Advantageously, the predefined mark may provide a feedback to users that are very strong or very weak, to help the users produce cement with the preselected viscosity and/or consistency.

In exemplary embodiments, cementitious material 358 is retained in chamber 310. Substance 358 is unable to fly-back through the mismatch zone, for example, as substance 358 is made up of large particles, too viscous, a solid, and/or otherwise lumped together. Advantageously, because the cementitious material is unable to fly-back, the method may be less messy and/or less risky, for example, the operator performing the method may not be splashed with the cementitious material.

Optionally, at 212, and as shown in FIG. 3F, cap 354 is removed from the distal end of applicator 300 after formation of cementitious material 358, for example, after compression and/or removal of excess fluid in box 210. Optionally, applicator 300 is hermetically sealed until removal of cap 354.

Advantageously, as the cap may only be removed once the cementitious material has been formed, there is no need for careful control to prevent leakage through an open end.

Optionally, at 214, and as shown in FIG. 3G, valve 314 and/or 316 are distally displaced so that cementitious material 358 exits from the distal end of applicator 300.

Optionally, formed cementitious material 358 has a substantially similar cross sectional size and shape as the inner wall of distal chamber 310.

Optionally, at 216, and as shown in FIG. 3H, formed cementitious substance 358 has been removed from applicator 300. Advantageously, material 358 has the right amount of water mixed therein, for example, the excess water having been automatically removed in box 208. Advantageously, material 358 is in a single workable piece, and not, for example, having been deformed and/or in a number of small unworkable pieces.

Optionally, the removed cementitious substance is used to treat bones and/or teeth of a patient. Optionally, the cementitious substance is used to repair bone and/or teeth defects, for example, by bone implantation, bone augmentation, and/or as a bone graft.

Mismatch Zones

FIGS. 4A-4E are some examples of mismatch zones, in accordance with exemplary embodiments of the invention. Illustrated are cross sectional views through the distal chamber of the dual component applicator (e.g., as shown in FIG. 1A), when one or both valves are in the distal chamber.

FIG. 4A is a cross sectional view of a distal valve 416 within a distal chamber 410 of the applicator. Note that a proximal valve (not shown) may lie behind distal valve 416 along a longitudinal axis of the applicator. Optionally, the area of the mismatch zone (e.g., as viewed in cross section) is not reduced by the sequentially arranged valves. As shown, chamber 410 has hexagonally shaped inner walls 450.

Optionally, valve 416 has a circular cross section so that the external perimeter of valve 416 is circumscribed within hexagon 450.

Optionally, several spaced apart passages, collectively referred to hereinabove as a mismatch zone 452 (shown as filled in areas), are formed by the mismatch in outer perimeter between the circle inscribed within the hexagon. As described hereinabove, the mismatch zone allows fluid (e.g., biocompatible fluid, air) flow from one chamber to another, for example, from the proximal chamber to the distal chamber and/or from the distal chamber to the proximal chamber.

Optionally, the valve(s) contact the inner walls of the chamber at least at 3 spaced apart regions. Optionally, the contact regions are spread around the circumference of the valve. Advantageously, the contact regions may guide the valve along within the chamber, in an axial manner, preventing tilting of the valve which may cause malfunction of the applicator.

Optionally, the area of one of the spaced apart passages forming the mismatch zone is about 1%-10% of the cross sectional area of the distal chamber, or about 1%-5%, or about 2%-5%, or other smaller, intermediate or larger percentages.

Optionally, any one of the passages forming the mismatch zone is small enough to prevent fly-back of the cementitious substance. Optionally, the passages are in fluid isolation from one another.

Optionally, the mismatch zone is large enough to allow fly-back of the excess fluid from the distal chamber during the mixing without having to apply pressure and/or causing a pressure strong enough to damage the applicator.

Optionally, the shape of the internal wall of the distal chamber is selected so that the shape does not structurally weaken the distal chamber. Optionally, the thickness of the barrel forming the distal chamber is thick enough at and/or near the passage of the mismatch zone so that the barrel is not structurally weakened. Optionally, the shape, material and/or thickness of the internal wall provides enough strength to resist breaking, cracking and/or leaking from pressures applied during operation of the applicator.

Some additional examples of possible mismatch zones are illustrated:

FIG. 4B is a cross sectional view of valve 416 within a distal chamber having a square cross sectional shape. A mismatch zone 456 is shown as a shaded region between the circle inscribed within the square.

FIG. 4C is a cross sectional view of valve 416 within a distal chamber having a circular cross sectional shape 458 with several spaced apart depressions 460 arranged along the inner circumference wall, the depressions being elongated in a direction coaxial to a longitudinal axis of the applicator. A mismatch zone is formed by depressions 460.

FIG. 4D is a cross sectional view of valve 416 within a distal chamber having a flower-like cross sectional shape 462. A mismatch zone 464 is formed within the pedals of the flower.

FIG. 4E is a cross sectional view of valve 416 within a distal chamber having an ellipse shaped 466 inner wall. A mismatch zone 468 is formed between the circle inscribed within ellipse 466.

Figure 5A:
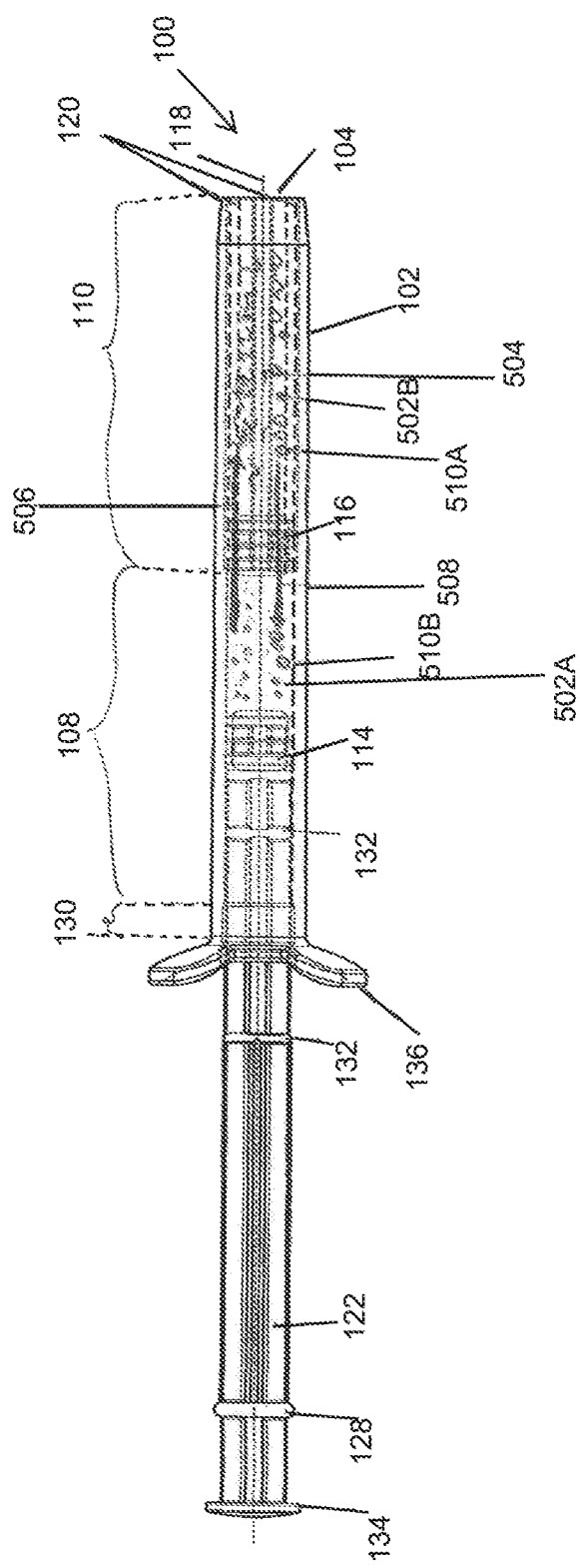
FIGS. 5A-5B are schematic illustrations of the applicator showing fluid flow through the mismatch zone, in accordance with exemplary embodiments of the invention.
Figure 5B:
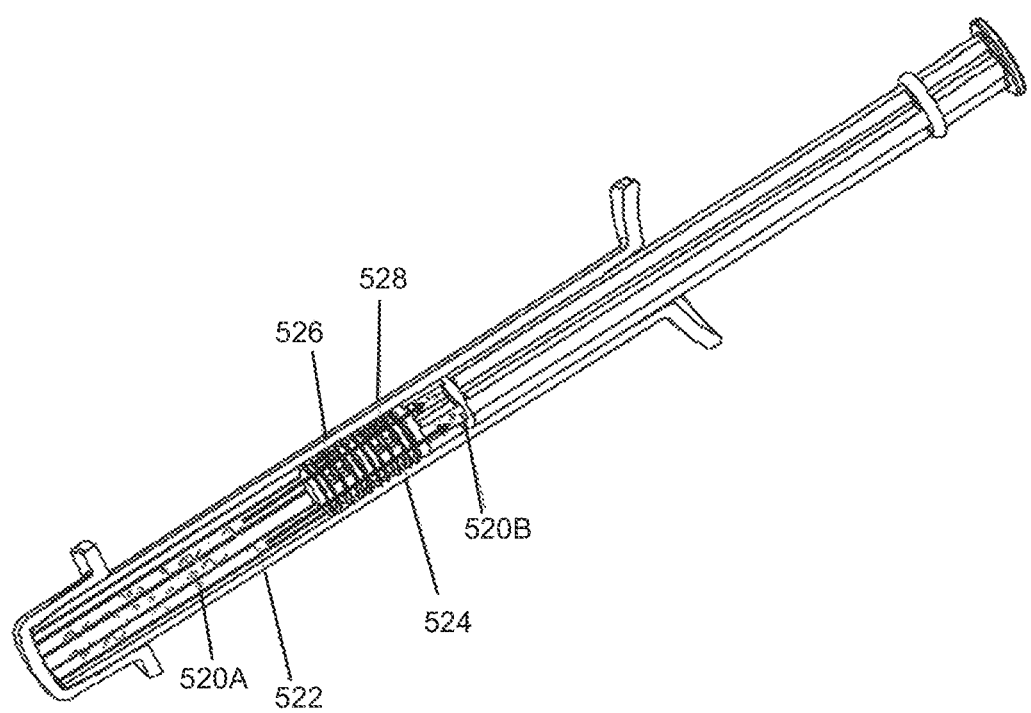

FIG. 5A-5B are schematic illustrations of the applicator, showing a side view of the fluid flow through the mismatch zone, in accordance with exemplary embodiments of the invention.

FIG. 5A is a schematic, for example, of applicator 100 of FIG. 1A. To help understand the state of the applicator, reference will be made to FIG. 3B, FIG. 2 box 206, and related descriptions. Fluid 502A (shown as filled in circles) flows from chamber 108 to chamber 110 (fluid 502B) through the mismatch zone, the fluid flow indicated by arrow 506. Fluid 502B mixes with pre-cementitious material 504 (shown as squiggly lines). Optionally, air 510A (shown as empty circles) is displaced by fluid 502B, and is flown-back through the mismatch zone to chamber 108 (shown as air 510B), the air movement through the mismatch zone indicated by arrow 508.

FIG. 5B is a schematic, for example, of applicator 100 of FIG. 1A. To help understand the state of the applicator, reference will be made to FIG. 3D, FIG. 3E, FIG. 2 box 208, and related descriptions. Fluid 520A (shown as filled in circles) has mixed with pre-cementitious material 522 (shown as squiggly lines) in the distal chamber.

Optionally, excess fluid 520B has been flown-back through the mismatch zone, the direction of the flying-back indicated by arrow 524. Optionally, the flying-back occurs through the mismatch zone formed by both a distal valve 526 and a proximal valve 528.

Assembly

FIG. 6A is an elevated view towards the front, showing the arrangement of the components of the applicator of FIG. 1A, in accordance with an exemplary embodiment of the invention. FIG. 6B is an elevated view towards the back of the applicator.

Optionally, a cap 602 seals the distal end of barrel 102. Optionally, cap 602 comprises one or more flanges 604, for example, providing the user with a grip to help remove cap 602. Optionally, cap 602 comprises one or more elevations 606 on the external surface. Advantageously, elevations 606 may help with removal of cap 602, for example, by allowing air to enter cap 602 through elevations 606 once the seal has been broken.

Optionally, the components are assembled as shown (e.g., following the dashed lines), for example, providing a method of assembling the applicator. The assembly may be performed, for example, at the factory (e.g., providing a pre-loaded applicator) and/or at the site of usage (e.g., dental office).

Optionally, the components are not bonded to one another. For example, the components are held together by frictional forces. Alternatively, one or more components are bonded together, for example, the proximal valve is glued to the distal end of the pushrod.

Other Views

FIGS. 7A-7E are schematic illustrations of various views the pre-loaded and/or assembled applicator, for example, of FIG. 1A (including the cap of FIG. 6A), in accordance with exemplary embodiments of the invention.

Arrow 700 indicates a perspective view.

Arrow 702 indicates an elevated side view.

Arrow 704 indicates an elevated side view with a 90 degree rotation of the view indicated by arrow 702.

Arrow 706 indicates an elevated side view with a 90 degree rotation of the view indicated by arrow 704.

Arrow 708 indicates an elevated side view with a 90 degree rotation of the view indicated by arrow 706.

Arrow 710 indicates a face-on and/or front view.

Arrow 712 indicates a back view.

FIGS. 8A-8C are cross sectional schematics corresponding to FIG. 7, showing internal components of the applicator, in accordance with exemplary embodiments of the invention.

Arrow 800 is a cross sectional view of the applicator as indicated by arrow 700 of FIG. 7.

Arrow 802 is a cross sectional view corresponding to arrow 702.

Arrow 804 is a cross sectional view corresponding to arrow 704.

Arrow 810 is a cross sectional view corresponding to arrow 710.

Arrow 812 is a cross sectional view corresponding to arrow 712.

FIGS. 9A-9E are schematic illustrations of various views of the applicator (e.g., of FIG. 1A), after having completed the mixing process and ejection of the mixed substance, in accordance with exemplary embodiments of the invention. To understand the state of the applicator as shown in FIGS. 9A-9E, reference may be made, for example, to FIG. 3H, FIG. 2 box 216, and related descriptions.

Arrow 900A indicates a perspective view of the applicator, after having completed the mixing process. Arrow 900B is a cross sectional view corresponding to the structure indicated by arrow 900A.

Arrow 902A indicates an elevated side view of the applicator indicated by arrow 900A. Arrow 902B is a cross sectional view corresponding to the structure indicated by arrow 902A.

Arrow 904A indicates an elevated side view of the applicator indicated by arrow 902A, rotated by 90 degrees. Arrow 904B is a cross sectional view corresponding to the structure indicated by arrow 904A.

Arrow 906 indicates a cross sectional view of the front of the applicator indicated by arrow 900A.

Arrow 908 indicates a cross sectional view of the back of the applicator indicated by arrow 900A.

Exemplary Materials

Optionally, the cementitious substance as described herein is used, for example, to treat bones deficiency and/or bone defects in the oral cavity, in maxillofacial surgical procedures, in orthopedic surgeries, in plastic surgeries and/or in oncologic bone reconstructions.

As described for example, in WO 2009/104187, co-invented by the present inventor, hereby incorporated by reference in its entirety, the present inventors have designed and prepared and practiced several compositions for bone augmentation, which include various specific combinations of calcium sulfate in different solid hydrate forms (also known as phases), which may, for example, harden with an aqueous environment in a relatively short setting time without compromising patient comfort. For example, a particular calcium sulfate phase combination and a particular particle size distribution ratio provide a bone grafting composition characterized by a unique setting time, rigidity and resorption period of the resulting bone graft. In another example, a bone graft composition which includes reinforcing materials which are currently used as dental and orthopedic bone grafts together with a matrix of calcium sulfate have been prepared. These compositions may provide strong hybrid bone graft materials which may be pliable, exhibit short setting times and/or a very rigid yet highly porous scaffold for bone grafts. These bone graft compositions may produce structures which are less brittle than those produced by the known reinforcing materials due to the calcium sulfate matrix that provides the compositions with the desired rigidity.

Optionally, the cementitious substance as described herein is used as a bone graft composition. Optionally, utilizing a mixture of a pre-cementitious substance and a non-cementitious substance, and further utilizing a unique particle size distribution of the particles of each of these substances, such that the composition comprises at least two different particle size ranges of the non-cementitious material. The unique particle size distribution of the compositions described herein, imparts to the compositions the desired properties demonstrated and described herein, and may advantageously render such compositions highly beneficial for bone augmentation procedures.

Optionally, the exemplary bone graft composition comprises a mass of particles of a pre-cementitious substance and a mass of particles of a non-cementitious substance, the mass of particles of the non-cementitious material being characterized by at least two non-overlapping ranges of particles size, the composition being characterized by a particle size distribution according to formula I:

$$T = a_0 S_0 + a_1 S_1 + a_2 S_2 + a_3 S_3 + a_4 S_4 + \ldots + a_i S_i + \ldots + a_n S_n \quad \text{Formula I}$$

wherein:

T is the particle size distribution of the composition;

$S_0$ is a particle size range of the pre-cementitious substance;

$a_0$ is a percentage by weight of the particles of the pre-cementitious substance of the total weight of the composition;

i is an integer ranging from 1 to n;

$S_1, S_2, S_3, \ldots S_i$ are each a particle size range of the non-cementitious substance;

at least two of the $S_1, S_2, S_3, \ldots S_i$ are non-overlapping particle size ranges;

$a_1, a_2, a_3, \ldots a_i$ are each a percentage by weight of the particles of the non-cementitious substance having the $S_1, S_2, S_3, \ldots S_i$ particle size range of the total weight of the composition, the pre-cementitious substance and the non-cementitious substance being selected such that upon contacting a mixture of both the substances with an aqueous solution, a biocompatible cementitious substance is formed.

Optionally, $S_0$ ranges from 0 µm to 500 µm;

$a_0$ ranges from 40 weight percents to 60 weight percents of the total weight of the composition; and a sum of $a_1, a_2, a_3, \ldots a_i$ ranges from 40 weight percents to 60 weight percents of the total weight of the composition.

Optionally, n=4; $S_1$ ranges from 800 µm to 1600 µm; $S_2$ ranges from 500 µm to 800 µm; $S_3$ ranges from 0 µm to 500 µm; and $S_4$ ranges from 0 µm to 100 µm.

Optionally, $S_0$ ranges from 0 µm to 100 µm; each of $a_1$ and $a_3$ ranges from 15 weight percents to 18 weight percents of the total weight of the composition; and each of $a_2$ and $a_4$ ranges from 7 weight percents to 10 weight percents of the total weight of the composition.

Optionally, the pre-cementitious substance includes calcium sulfate hemihydrate (CSAccording to some embodiments of the invH).

Optionally, the non-cementitious substance is selected from the group consisting of a highly-resorbable substance, a poorly-resorbable substance and a combination thereof.

Optionally, the non-cementitious highly-resorbable substance includes calcium sulfate dihydrate (CSD).

Optionally, the poorly-resorbable substance is selected from the group consisting of beta-tricalcium phosphate (β-TCP), hydroxylapatite (HA), bovine-derived hydroxylapatite, porous coralline hydroxylapatite, calcified algae, synthetic particulate glass ceramic, bioactive glass, autogenic bone shavings, allogeneic cancellous bone, irradiated cancellous allogeneic bone, anorganic bovine bone, composites of polymer and calcium hydroxide and any combination thereof.

Optionally, the pre-cementitious substance includes calcium sulfate hemihydrate (CSH) and the non-cementitious includes calcium sulfate dihydrate (CSD).

Optionally, the pre-cementitious substance includes calcium sulfate hemihydrate (CSH) and the non-cementitious includes calcium sulfate dihydrate (CSD) and beta-tricalcium phosphate (β-TCP).

Optionally, $S_0$ ranges from 0 μm to 100 μm; $a_0$ is about 50 weight percents of the total weight of the composition; n=4; $S_1$ ranges from 800 μm to 1600 μm; $S_2$ ranges from 500 μm to 800 μm; $S_3$ ranges from 0 μm to 500 μm; $S_4$ ranges from 0 μm to 100 μm; each of $a_1$ and $a_3$ is independently about 16.5 weight percents of the total weight of the composition; and each of $a_2$ and $a_4$ is independently about 8.5 weight percents of the total weight of the composition.

Optionally, the composition presented herein is capable of forming a cured cementitious substance.

Optionally, the cementitious substance is characterized by a setting time which ranges from 1 minute to 1.5 minutes.

Optionally, the cementitious substance is being pliable and malleable for a time period of from 2 minutes to 4 minutes.

Optionally, the cured cementitious substance is characterized by a porosity that ranges from 40% to 60% by volume.

Optionally, the cured cementitious substance is characterized by a resorption period that ranges from 4 to 10 weeks.

Optionally, the cured cementitious substance is characterized by a compressive strength that ranges from 7 MPa to 15 MPa.

Optionally, the cured cementitious substance is characterized by an elastic modulus that ranges from 500 MPa to 1000 MPa.

Additional exemplary pre-cementitious substances that can be suitable for use in the context of embodiments of the invention include, but are not limited to, calcium hydroxide, various forms of calcium silicates, various natural and fabricated pozzolans, fly ash, silica fume, various polymers and combinations thereof.

Another example of a material that may be formed by mixing using embodiments of the applicator described herein in described in U.S. Patent Application No. 2004/0254259, hereby incorporated by reference in its entirety, is a polymer containing calcium sulfate particles as an implant material, comprising a calcium sulfate compound selected from the group consisting of calcium sulfate dihydrate, calcium sulfate hemihydrate and mixture thereof, coated with at least one resorbable polymer selected from the group consisting of poly(desaminotyrosyl-tyrosine alkyl ester carbonate) and aliphatic polyester of alpha-hydroxy acid derivatives, with a coating thickness from about 2 μm to about 50 μm to control resorption rate of the calcium sulfate compound.

Another example of a material that may be formed by mixing using embodiments of the applicator described herein in described in U.S. Pat. Nos. 7,371,408, 7,371,409, and 7,371,410, hereby incorporated by reference in its entirety, comprises, in general, calcium sulfate; a mixing solution such as sterile water; and a plasticizing substance such as carboxymethylcellulose. For example, the bone graft substitute composition comprises: about 80 to about 120 parts by weight of calcium sulfate; about 10 to about 100 parts by weight of demineralized bone matrix; about 20 to about 130 parts by weight of cancellous bone; about 1 to about 40 parts by weight of a plasticizing substance; and about 21 to about 250 parts by weight of a mixing solution, wherein the cancellous bone has a particle size between about 1 and about 4 mm. Or, for example, the bone graft substitute composition comprises calcium sulfate; a mixing solution selected from the group consisting of sterile water, sodium chloride, phosphate buffered saline, potassium chloride, and sodium sulfate; and a plasticizing substance selected from the group consisting of carboxymethylcellulose, polyvinyl alcohol, methycellulose, and hydroxypropyl methylcellulose.

Another example of a material that may be formed by mixing using embodiments of the applicator described herein in described in U.S. Pat. No. 5,281,265, hereby incorporated by reference in its entirety, appears to teach that a calcium ion can react with a citrate ion to form a less soluble calcium citrate salt, thus forming cement. The patent further appears to teach a bone cement material comprising calcium sulfate components, wherein the interaction of a calcium-containing cementing component and a setting component produces a calcium-containing cement which has reduced solubility in water relative to the calcium-containing cementing component. Useful cementing components appear to be taught therein are calcium sulfate dihydrate, calcium sulfate hemihydrate and anhydrous calcium sulfate. The cement taught therein may be dried after its preparation, and broken into particles, to form suitable sized particles such as granules. The described material comprises a surgical cement for use in medical applications such as orthopedic and maxillofacial surgeries and dental applications comprising a hardened cement formed from a mixture comprising a cementing component selected from the group consisting of calcium sulfate-containing components, calcium succinate, calcium malate, calcium malonate, calcium maleate, hydrates thereof and mixtures thereof, the cementing component having a solubility in water at 25 0.5.times.10.sup.-2 M to about 20 selected from the group consisting of water soluble, neutral salts of polyfunctional carboxylic acids containing 2 to about 10 carbon atoms, water soluble dibasic phosphate salts and mixtures thereof; and water in an amount effective to form a paste from the mixture which paste hardens into the hardened cement which is biocompatible, provided that the weight ratio of the cementing component to the setting component in said mixture is in the range of about 1:1 to about 5:1.

Another example of a material that may be formed by mixing using embodiments of the applicator described herein in described in International Patent Application Publication No. WO 2007/046109, of which one of the present inventors is a co-inventor, hereby incorporated by reference in its entirety, appears to teach bone grafting compositions which comprise flakes made of a mixture CSH and CSD, which exhibit both the cementitious and binding properties of CSH and the strength and longer resorption period of the rigid CSD and tricalcium phosphate (TCP) granules. The substance is a composition-of-matter comprising a flake, the flake comprises a first agent having a first pre-determined resorbability rate under physiological conditions and a second agent having a second pre-determined resorbability rate under physiological conditions, the second resorbability rate being different than said first resorbability rate.

Another example of a material that may be formed by mixing using embodiments of the applicator described herein in described in International Patent Application Publication No. WO 2000/045734, hereby incorporated by reference in its entirety, appears to teach a composite, which can be used for filling in bone voids, and which comprise various forms of calcium sulfate hemihydrate, calcium sulfate dihydrate, or combinations thereof. The composite has a controlled rate of dissolution. The composite includes (a) a first region that includes a first composition that includes calcium sulfate, the first region exhibiting a first rate of dissolution; and (b) a second region that includes a second composition that includes calcium sulfate, the second region exhibiting a second rate of dissolution, the first rate of dissolution being different from the second rate of dissolution.

Another example of a material that may be formed by mixing using embodiments of the applicator described herein in described in International Patent Application Publication No. WO 2000/027316, hereby incorporated by reference in its entirety, refers to surgical cement, composed mainly of a calcium sulfate salt, for example calcium sulfate dihydrate, calcium sulfate hemihydrate, anhydrous calcium sulfate and mixtures thereof.

Another example of a material that may be formed by mixing using embodiments of the applicator described herein in described in U.S. Patent Application No. 2003/0167093, hereby incorporated by reference in its entirety, relates to a bone replacement material based on combination of calcium phosphate compounds, comprising at least two fillers with different in vivo dissolution rates, wherein the compound with the higher dissolution rate will dissolve and create pores for bony ingrowth, and whereas the compound with the lower dissolution rate will still provide strength and toughness reinforcement to the composition, and will only dissolve at a later stage, when more bony material has been formed to support the bone structure, to create additional pores.

Another example of a material that may be formed by mixing using embodiments of the applicator described herein in described in International Patent Application Publication No. WO 2008/094585, hereby incorporated by reference in its entirety, which appears to teach a method for facilitating bone repair by providing calcium sulfate hemihydrate particles, wherein at least 50% of the particles have a diameter of 50 to 500 nanometer, mixing the particles with an aqueous solution to obtain a paste, applying the paste to an area of bone in need of repair, and allowing the paste to set.

It is expected that during the life of a patent maturing from this application many relevant dual component applicators will be developed and the scope of the term dual component applicator is intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A mixing applicator for mixing a fluid substance with a solid substance to obtain a resulting substance having a desired consistency, the applicator comprising:

a hollow elongated barrel having distal and proximal openings, the elongated barrel having a first cross sectional shape along a first proximal portion of the elongated barrel defining a first chamber, and a different second cross sectional shape along a second distal portion of the elongated barrel defining a second chamber, the second cross sectional shape extending from the distal end of the first portion to the distal opening of the hollow elongated barrel;

a solid substance;

a liquid substance;

a first and a second valve both slidably displaceable within the hollow elongated barrel and sequentially arranged along a longitudinal axis of the hollow elongated barrel, said solid substance and said fluid substance being separately held on either side of said second valve, the first and second valves having a third cross-sectional shape being complementary to said first cross sectional shape, thereby providing fluid-tight engagement within said first cross-sectional shape, said third cross-sectional shape being mismatched with said second cross-sectional shape to form a mismatch zone along a length of said second chamber, said mismatch zone allowing fluid flow around the valves, said valves being slidable along a length selected to locate all three of said solid substance, said second valve and said fluid substance together in said mismatch zone, thereby to allow said first and second valves to effect mixing of said fluid substance with said solid substance and subsequently to remove excess fluid to obtain said resulting substance having said desired consistency, wherein the third cross-sectional shape of both the first and second valves comprise a circular cross-sectional shape and the second cross-sectional shape of the second chamber comprises a hexagonal cross-sectional shape, the hexagonal cross-sectional shape providing said mismatch and allowing said mixing.

2. The applicator of claim 1, wherein the first and second valves contact an internal wall of the second chamber at least at 3 spaced apart areas.

3. The applicator of claim 1, wherein an area of a spaced apart passage of the mismatch zone is about 1%-5% of the cross sectional area of the second chamber.

4. The applicator of claim 1, wherein the first and second valves are sized and shaped for forming the fluid-tight engagement between an external perimeter of the valves and an internal wall of the first chamber, and for forming the mismatch zone between the external perimeter of the valves and an internal wall of the second chamber.

5. The applicator of claim 1, wherein the fluid substance is a biocompatible fluid and the solid substance is a pre-cementitious material that forms a cementitious material upon mixing with the biocompatible fluid.

6. The applicator of claim 1, wherein the solid substance is a bone graft composition comprising a plurality of particles of a pre-cementitious substance and a plurality of particles of a non-cementitious substance, wherein the plurality of particles of the non-cementitious substance is characterized by at least two non-overlapping ranges of particle size, the composition being characterized by a particle size distribution according to formula I:

$$T = a_0 S_0 + a_1 S_1 + a_2 S_2 + a_3 S_3 + a_4 S_4 + \ldots + a_i S_i + \ldots + a_n S_n \quad \text{formula I}$$

wherein:

T is the particle size distribution of the composition;

$S_0$ is a particle size range of the pre-cementitious substance;

$a_0$ is a percentage by weight of the particles of the pre-cementitious substance of the total weight of the composition;

i is an integer ranging from 1 to n;

$S_1, S_2, S_3, \ldots S_i$ are each a particle size range of the non-cementitious substance;

at least two of the $S_1, S_2, S_3, \ldots S_i$, are non-overlapping particle size ranges;

$a_1, a_2, a_3, \ldots a_i$, are each a percentage by weight of the particles of the non-cementitious substance having the $S_1, S_2, S_3, \ldots S_i$, particle size range of the total weight of the composition, the pre-cementitious substance and the non-cementitious substance being selected such that upon contacting a mixture of both the substances with an aqueous solution, a biocompatible cementitious material is formed.

7. The applicator of claim 1, wherein a fit between the third-cross sectional shape and the second cross-sectional shape in the mismatch zone is configured to be sufficient for the valves to seal against the solid and the resulting substance.

8. The applicator of claim 1, wherein the length of the internal wall of the second chamber when measured along a longitudinal axis of the barrel is longer than the combined lengths of the first and second valves.

9. The applicator of claim 1, wherein the distal opening of the hollow elongated barrel has a fourth cross-sectional shape that is substantially the same as the second cross-sectional shape of the second chamber.

10. The applicator of claim 1, wherein the barrel is made out of a transparent material.

11. The applicator of claim 1, wherein the first and second valves are made out of a material that is resistant to sterilization methods.

12. The applicator of claim 11, wherein the material is plastic.

13. The applicator of claim 1, further comprising a rod in mechanical communication with the first valve so that displacement towards a distal end of the rod distally displaces the first valve, the second valve being distally displaced by mechanical contact exerted by the first valve.

14. The applicator of claim 9, wherein the fourth cross-sectional shape of the distal opening is too large for direct injection of the resulting substance for use inside a body of a patient.

15. The applicator of claim 9, wherein the fourth cross-sectional shape of the distal opening is too large for attachment to a needle used to inject substances into the body.

16. The applicator of claim 9, further comprising a cap having an internal cross sectional size and shape to seal the distal opening.

* * * * *